United States Patent [19]

della-Cioppa et al.

[11] Patent Number: 5,801,047

[45] Date of Patent: *Sep. 1, 1998

[54] METHOD FOR MAKING STABLE EXTRACELLULAR TYROSINASE AND SYNTHESIS OF POLYPHENOLIC POLYMERS THEREFROM

[75] Inventors: Guy Richard della-Cioppa; Stephen John Garger, Jr.; Richard Barry Holtz; Michael Jay McCulloch; Genadie Gleb Sverlow, all of Vacaville, Calif.

[73] Assignee: Biosource Technologies, Inc., Vacaville, Calif.

[ * ] Notice: The term of this patent shall not extend beyond the expiration date of Pat. Nos. 5,340,734 and 5,792,649.

[21] Appl. No.: 471,993

[22] Filed: Jun. 6, 1995

Related U.S. Application Data

[60] Continuation of Ser. No. 154,283, Nov. 17, 1993, which is a division of Ser. No. 982,095, Nov. 25, 1992, Pat. No. 5,340,734.

[51] Int. Cl.$^6$ .................... C12N 1/20; C12N 9/96
[52] U.S. Cl. .................. 435/253.6; 435/188; 435/184
[58] Field of Search .................... 435/69.1, 252.3, 435/320.1, 189, 212, 125, 188, 253.6; 536/22.1, 23.1; 528/207, 208, 210

[56] References Cited

FOREIGN PATENT DOCUMENTS 0 441 689 A1  2/1991  European Pat. Off. .
WO 92/00373  1/1992  WIPO .

OTHER PUBLICATIONS

Baumann et al., 1976, "Control of Melanin Formation in *Streptomyces Glaucescens*," *Actinomycetes the Boundary Microorganisms*, Tokyo: Toppan Co. 55–63 (Arai, T., ed.).
Bernan et al., 1985, "The Nucleotide sequence of the tyrosinase gene from *Streptomyces antibioticus* and characterization of the gene product," *Gene* 37:101–110.

Billmeyer and Saltzman, 1981, *Principles of Color Technology*, 2nd ed.
Crameri et al., 1982, "Secretion of tyrosinase in *Streptomyces glaucescens*," *J. Gen. Microbiol.* 128:371–379.
Crippa et al., 1989, "Chemistry of Melanins," *The Alkaloids* 36:254–322.
Doddema, H.J., 1988, "Site–Specific Hydroxylation of Aromatic Compounds by Polyphenol Oxidase in Organic Solvents and in Water," *Biotech. & Bioeng.* 32:716–718.
Gardner et al., 1987, "Expression of tyrosinase in recombinant Streptomyces," *Abstract Papers, Am. Chem. Soc.* 194 Meet, MBTD101.
Gardner & Cadman, 1990, "Product Deactivation in Recombinant Streptomyces," *Biotechnology and Bioengineering* 36:243–251.
Hayaishi, O., 1968, in Biological Oxidation (Singer, R.P., ed.), Interscience Publishers, New York 581–601.

(List continued on next page.)

*Primary Examiner*—Charles L. Patterson, Jr.
*Attorney, Agent, or Firm*—Albert P. Halluin; Howrey & Simon

[57] ABSTRACT

A process for the in vitro production of chemically modified polyphenolic polymer (PPP). First, stable, highly active extracellular tyrosinase is produced from genetically transformed microorganism such as *Streptomyces antibioticus*. The tyrosinase is then incubated with a reaction substrate such as 1-tyrosine, hydrolyzed protein, or an oligopeptide in combination with 1-tyrosine. The ratio of the oligopeptide/ tyrosine combination as well as variation in the concentration of tyrosinase can be used to modify the color, the molecular size, and the spectral absorbance properties of the PPP produced. Alternatively, or additionally, oxidants such as hydrogen peroxide or hypochlorite can be used to modify the color of the PPP, regardless of the method used to produce the PPP, and the PPP can subsequently be fractionated using molecular weight cut-off ultrafiltration. Organic solvents can also be used in the method of making PPP to produce PPPs having variable but reproducible physical properties.

6 Claims, 5 Drawing Sheets

OTHER PUBLICATIONS

Katz, E. et al., 1983, "Cloning and Expression of the Tyrosinase Gene from *Streptomyces antibioticus* in *Streptomyces lividans*," *J. Gen. Microbio.* 129:2703–2714.

Katz & Betancourt, 1988, "Induction of tyrosinase by $_L$–methionine in *Streptomyces antibiotcus*," *Can. J. Microbiol.* 34:1297–1301.

Kawamoto et al., 1993, "Cloning, sequence and expression of the tyrosinase gene from *Streptomyces lavendulae* MA406 A–1," *Journal of Fermentation and Bioengineering* 76(5):345–355.

Kibanov, Alexander M., 1986, "Enzymes that work in organic solvents," *Chemical* June:354–359.

Lee et al., 1988, "A trans–acting gene is required for the phenotypic expression of a tyrosinase gene in Streptomyces," *Gene* 65:71–81.

Lerch, Konrad, 1981, "Copper Monooxygenases: Tyrosinase and Dopamine β–Monooxygenase," *Met. Ions. Biol. Syst.* 13:144–186.

Lerch and Ettinger, 1972, "Purification and Characterization of a Tyrosinase from *Streptomyces glausescens*," *Eur. J. Biochem* 31:427–437.

Mason, H., 1947, "The Chemistry of Melanin," *J. Biol. Chem.* 168:433–438.

Milstein et al., 1989, "Oxidation of aromatic compounds in organic solvents with laccase from *Trametes versicolor*," *Appl. Microbiol. Biotechnol.* 31:70–74.

Morino et al., 1988, "Enterspecific transfer and expression of melanin gene(s) on cosmids in Streptomyces strains," *Appl. Microbiol. Biotechnol.* 27:517–520.

Pirt et al., 1970, "Melanin production in *Aspergillus nidulans*," *Chemical Abstracts* 72:No. 1, 878d.

Prota, G., 1988, "Progress in Chemistry of Melanins and Related Metabolities," *Med. Res. Rev.* 8:525–556.

Raper, Henry S., 1927, "The Tyrosinase-Tyrosine Reactions," *Biochem. J.* 21:89–96.

Wilczok et al., 1984, "Spectroscopic Studies of Chemistry Modified Synthetic Melanins," *Arch. Biochem. Biophys* 231:257–262.

Wolfram et al., 1970, "The Mechanism of Hair Bleaching," *J. Soc. Cosmt. Chem.* 21:875–900.

Yasunobu et al., 1959, "The Oxidation of Tyrosine–containing Peptides by Tyrosinase," *J. Biol. Chem.* 234:3291–3205.

Yoshimoto T., et al., 1985, "Extracellular Tyrosinase from Streptomyces Sp. KY–453: purification and Some Enzymatic properties," *J. Biochem* 97:1747–1754.

METHOD FOR MAKING STABLE EXTRACELLULAR TYROSINASE AND SYNTHESIS OF POLYPHENOLIC POLYMERS THEREFROM

This is a continuation of application Ser. No. 08/154,283 filed Nov. 17, 1993 which is a division of application Ser. No. 07/982,095 filed Nov. 25, 1992, now U.S. Pat. No. 5,340,734.

BACKGROUND OF THE INVENTION

Melanin is an omnibus term that describes a large family of natural and synthetic phenolic-quinonoid pigments of diverse origin and chemical nature. Natural melanins are generally differentiated by their origin, for example, bovine eye melanin, melanoma melanin, and sepia melanin. They usually occur in the form of granular particles and are secretory products of pigment-producing cells, the melanocytes. Synthetic melanins are named after the compound from which they were prepared via chemical or enzymatic oxidation (e.g., d,l-dopa., or 5,6-dihydroxyindole catechol melanin). In addition, melanins are classified according to their chemical structures into the insoluble black eumelanins (poly-5,6-indole quinones) and the alkali soluble red phaeomelanins (polydihydrobenzothiazines).

The study of melanins has led to the discovery of a number of biosynthetic pathways. For example, melanins can be produced by the oxidation of its precursors such as 1-dopa or tyrosine by a melanin-synthesizing enzyme, tyrosinase. Alternatively, melanin can be prepared chemically by auto-oxidation of 1-dopa or other substrates to melanin in the presence of atmospheric oxygen. Wilczok et al., *Arch Biochem. Biophys.* 23: 257 (1984). Additionally, melanin can be prepared by a variety of electrochemical and photochemical methods from which individual steps of the melanization processes are identified and characterized. See, Crippa, et al. (1989), supra.

When melanin shows a characteristic UV absorption spectrum at a particular range of wavelengths, it is assumed that the melanin may exert a protective effect by absorbing or diminishing the energy generated by the correspondent wavelengths. In general, sunlight contains three types of ultraviolet wave lengths which may cause skin damage. UV A has the longest wave length and the lowest energy. Its wavelengths fall within the range of 320–400 nm, and such wavelengths can indirectly damage DNA by activating intracellular flavins or porphyrins in the formation of active oxygen species, e.g., hydrogen peroxide, hydroxyl radicals, oxygen radicals, etc. UV B falls within the range of 290–320 nm. It damages DNA both directly and indirectly. This type is probably the major causative factor in skin cancer. UV C has wavelengths between 200–290 nm. Its major effect is directly related to damage of cellular DNA.

Characteristics of light relevant here fall into two major categories: (1) luminous flux which is the effectiveness of light evoking brightness; (2) chromaticity which is referred to both the dominant wavelength that contributes to the actual color (i.e., hue) and the purity that establishes the saturation of color. The spectrum colors and their wavelengths are further categorized as the follows: violet (400 nm), blue (450 nm), green (500 nm), yellow (550 nm), orange (600 nm) and red (650 nm).

The enzymatic synthesis of melanin has been an area of extensive research due to its close resemblance to natural melanogenesis. The enzymes, tyrosinases, are widely distributed in nature and highly purified preparations have been obtained from mushrooms, (Lerch, K, *Met. Ions. Biol. Syst.* 13: 144 (1981)), *Neurospora crassa, Podospora anserina*, potato tubers, broad beans, insect hemolymph and mammalian melanoma tumors. Lerch, K. and L. Ettlinger, *Eur. J. Biochem.* 31: 427–437 (1972). It is generally agreed that these enzymes catalyze two types of reactions: the orthohydroxylation of monophenols to catechols, which is referred to as cresolase activity, and the dehydrogenation of catechols to o-quinones, designated as catecholase activity. Molecular oxygen is used for the hydroxylation reaction. For this reason, tyrosinase acting on a monophenol is referred to as a "mixed function oxidase". Hayaishi, O. in *"Biological Oxidation"* (Singer, T. P., ed.) p.581, Interscience Publishers, New York (1968).

Numerous investigations have revealed that the production of tyrosinase by a microorganism in a growth medium is regulated by such factors as the genetics of the microorganism, the composition of the medium, the growth temperature, the presence of biosynthetic inhibitors, the density of tyrosinase-producing cells and the presence of enzyme inducers. Katz, E. and A. Betancourt, *Can J. Microbiol.* 34: 1297–1303 (1988). Some microorganisms are capable of producing extracellular tyrosinases which are synthesized intracellularly prior to their transport and secretion into the growth medium. Baumann, R., et al., *Actinomycetes "The Boundary Microorganisms"*, pp.55–63, (Arai, T. ed), Tokyo Joppan Co. (1976).

The discovery of extracellular tyrosinase makes industrial pigment production by fermentation feasible. However, the high instability of the extracellular tyrosinase in the broth limits the recovery of active tyrosinase in these processes and hence limits production of melanin. Bauman, R. et al., (1976), supra. Moreover, the quantities and recovery of the secreted extracellular tyrosinases have been generally insufficient for a viable commercial process for the large-scale in vitro production of melanin. Loss of enzyme activity as a result of deactivation through the affects of oxygen, temperature and product intermediates has a severe affect on the yield of tyrosinase and, therefore, is responsible for the high instability and low yield of extracellular tyrosinase. Studies in *Streptomyces antibioticus* have shown that the kinetics of the loss of tyrosinase activity could be approximated by a first-order model, with a constant specific deactivation rate on the order of $0.1h^{-1}$. Proteolytic activity detected in stationary phase cultures suggested that proteolytic degradation of tyrosinase could be partly responsible for the loss of tyrosinase activity during this period of batch cultures, but tyrosinase deactivation was also observed during the growth phase when no proteolytic activity was detected. The specific deactivation rate was found to exhibit an Arrhenius dependence on temperature with an activation energy of approximately 20 kcal/mol. Growth of a culture using a two-temperature strategy along with an enriched growth medium resulted in a 2.5-fold increase in the amount of tyrosinase obtained over control cultures. Gardner, A. R. and T. W. Cadman, *Biotechnology and Bioengineering* 36: 243–251 (1990). Improved processes for making tyrosinase and melanin are disclosed in PCT publication W092/00373 dated Jan. 9, 1992, which claims priority from U.S. Ser. Nos. 545,075, Jun. 29, 1990 and 607,119, Nov. 2, 1990, the disclosures of which are each incorporated by reference herein.

In addition to growth manipulation and temperature optimization, several microorganisms may be genetically engineered to further enhance their abilities to produce tyrosinases. These microorganisms include, but are not limited to species of Streptomyces, Escherichia, Bacillus, Streptococcus, Salmonella, Staphylococcus, and Vibrio. Many species of Streptomyces are capable of forming dark melanin pigments due to expression of tyrosinase from the mel gene locus. For example, the mel locus of S. antibioticus has been cloned and sequenced, Katz, E., et al., J. Gen. Microbiol. 123: 2703 (1983); Bernan, V. et al., Gene 37: 101 (1985) and shown to contain two open reading frames (ORFs) that encode a putative ORF438 protein (MW=14, 754) and tyrosinase (MW=30,612). ORF438 and tyrosinase are thought to be transcribed from the same promoter in S. antibioticus, and both genes are required for melanin production. Bernan, V., et al., (1985), supra. Based on genetic evidence, the ORF438 protein has been shown to function as a trans-activator of tyrosinase. Lee, Y.-H. W. et al., Gene 65: 71 (1988). It has been suggested that the ORF438 protein is involved in tyrosinase secretion, or it may function as a metallothionein-like protein that delivers copper to apotyrosinase. Bernan, V., et al., (1985), supra; Lee Y.-H. W., et al., (1988), supra.

The oxidation of a variety of N-terminal, C-terminal, and internal tyrosine peptides of melanin in the presence of mushroom tyrosinase has been studied spectrophotometrically. The spectroscopic patterns of these oxidations fall into three types: a dopachrome sequence, a dopa-quinone sequence, and a protein sequence. The dopachrome pattern is characterized by the formation of an intermediate oxidation product with absorption maxima at 305 nm and 480 nm. This absorption spectrum is exhibited by compounds of the aminochrome class, especially by dopachrome itself. The final oxidation product shows a maximum at 325 nm. This is very similar to the maximum at 319 nm exhibited by derivatives of 2-carboxy-5,6-dihydroxyindole, which is an intermediate in the enzymatic oxidation of 3,4-dihydroxyphenylalanine under conditions in which decarboxylation does not take place. Compounds which show the dopachrome pattern upon oxidation have blocked carboxyl groups and cannot undergo decarboxylation. It is accordingly probable that the development of the 325 nm absorption band is due to the accumulation of a derivative of 2-carboxy-5,6-dihydroxyindole. The dopaquinone pattern is characterized by the formation of an intermediate oxidation product with an absorption maximum at 390 nm. The protein pattern of oxidation, which is observed with a polypeptide which contains tyrosine may vary, depending upon the particular substrate. The distinctive absorption patterns, therefore, may be used to evaluate the positions of tyrosine in the peptide chains. Yasunobu, K. T., et al., J. Biol Chem. 234: 3291–3205 (1959).

Similar spectrophotometrical studies have been conducted on melanin for the enzymatic oxidation of a single amino acid in the presence of tyrosinase. The process was observed to proceed in three chromophoric phases, the first corresponding to the formation of the red pigment, the second to an intermediate purple pigment, and the third to the formation of melanin. By comparison of the observed spectra of these products with those of known substances, it is possible to identify the intermediates during the process of melanin formation. Mason, H. S., J. Biol. Chem., 168: 433 (1947); Raper, H. S., Biochem. J., 21: 89–96 (1927).

Recently it has been shown that a number of enzymes can express their activity in reaction media where most of the water has been replaced by an organic solvent. Kibanov, A. M. Chemtech June, 354–359 (1986). For example, laccase purified from Trametes versicolor can oxidize 2,6-dimethoxyphenol and syringaldazine in hydrophobic solvents presaturated with water. Milstein et al., Appl. Microbiol. Biotechnol 31: 70–74 (1989). In addition, the ortho-hydroxylation of aromatic compounds by the enzyme polyphenol oxidase such as tyrosinase suspended in organic solvents has also been found to be efficient. Doddema, H. J. Biotechnology and Bioengineering 32: 716–718 (1988). However, some of the reported prior art methods require the enzymes to be immobilized on an inert surface or carrier prior to enzymatic reaction conducted in organic solvents.

In addition to tyrosinase, a number of other enzymes possessing a peroxidizing activity such as horseradish peroxidase, chloroperoxidase, milk peroxidase, cytochrome C peroxidase and microperoxidase have also been used to produce melanin in vitro. These methods generally require the inclusion of hydrogen peroxide as a substrate in the reaction mixture and, in some instances, the immobilization of peroxidase prior to the oxidation reactions. European Patent Publication No. 441, 689 A1. However, the in vitro synthesis of melanin under such harsh conditions has not been described or suggested when tyrosinases are used as the enzyme sources.

In light of the foregoing, there is a need for an improved method for the production of stable and highly active extracellular tyrosinase in commercially acceptable quantities. There is a further need to develop an improved in vitro process for the synthesis of melanins (hereafter polyphenolic polymers or "PPPs" ) generally and chemically modified PPPs specifically in the absence of a fermentation medium and microorganisms. This need is driven by the advantages that such an in vitro process would provide, i.e. eliminating the concern about using precursers in the reaction which would be toxic if used in vivo, and the avoidance of complications arising from the presence of cellular metabolites and debris.

SUMMARY OF INVENTION

To achieve this end, a first aspect of the present invention relates to a novel method for the in vivo production of commercial quantities of a stable, highly active, extracellular tyrosinase. Any transformed microorganism which contains an expression vector containing genetic sequences encoding for tyrosinase may be used, so long as the microorganism is capable of expressing and secreting functional tyrosinase into the media. The method further comprises the steps of causing the microorganism to express extracellular tyrosinase, and recovering the extracellular tyrosinase from the cellular debris by filtration or centrifugation.

A second aspect of the invention relates to methods for stabilizing the extracellular tyrosinase so produced by means of low temperature storage, with or without a preservative and/or using an inert gas to replace air surrounding the tyrosinase, or freeze drying. Because the tyrosinase can be stored for extended periods of time, such as for more than a year, the method provides a particularly useful means for providing the necessary availability of large quantities of tyrosinase needed for a variety of end uses as discussed in detail below.

In a third aspect of the invention, PPPs are produced without fermentation, in either aqueous or organic solutions, using tyrosinase mediated polymerization of tyrosine, hydrolyzed proteins, tyrosine derivatives, and tyrosine-containing oligopeptides including tyrosine dipeptides and mixtures thereof. Since the color of PPPs varies with chemical and physical characteristics such as the UV and visible absorbance spectra, molecular size, aqueous solubility and substrate chemistry, such PPPs may possess different reproducible characteristics such as different colors.

In a fourth aspect of the invention the color of the PPP made from the same substrate/1-tyrosine combination can be modified by varying the ratio of each substrate/1-tyrosine combination. Similarly, the color of PPP that derives from the same substrate/1-tyrosine combination can be varied to produce different colors by reacting the substrate/1-tyrosine combination with different concentrations of tyrosinase.

In a fifth aspect of the invention, the color of such PPPs (whether produced by the method noted or other known methods) can be modified by use of a strong oxidizing reagent, such as hydrogen peroxide, hypochlorite, peracetic acid, perchloric acid, or potassium permanganate (Wolfram et al. (1970) J. Soc. Cosmet. Chem. 21: 875–900), and subsequently recovered by ultrafiltration.

In light of this, the present invention is, in its broadest form, an in vivo method of producing a stable extracellular tyrosinase, comprising the steps of growing a transformed microorganism which contains an expression vector containing genetic sequences encoding for tyrosinase under suitable growth media and conditions; causing the microorganism to express extracellular tyrosinase; and recovering the extracellular tyrosinase from the cellular debris by filtration or centrifugation.

In a more specific form, the method can include the further step of stabilizing the recovered extracellular tyrosinase by freeze-drying the tyrosinase, or by storing the tyrosinase at a temperature of 22° C. or less, or preferably at a temperature of 4° C. or less, using a protectant and, if desired, in an inert gas atmosphere.

The method of growing the transformed microorganism can include the step of preparing an expression vector, where the vector used is the plasmid pBS1082S. The host microorganism for the method can be selected from Streptomyces, Escherichia, Bacillus, Streptococcus, Salmonella, Staphylococcus, and Vibrio, and is preferably Streptomyces, and most preferably *Streptomyces antibioticus* IMRU 3720.

During the process of making tyrosinase controlling the amount of dissolved oxygen in the mixture can be used to cause the microorganism to express extracellular tyrosinase in a timely and efficient manner.

The invention further relates to an in vitro method of producing polyphenolic polymers ("PPPs"), and the PPPs made from that method, comprising the steps of contacting extracellular tyrosinase and a reaction substrate selected from the group consisting of 1-tyrosine, hydrolyzed protein, X/1-tyrosine, and 1-tyrosine/X, where X is a single amino acid, a dipeptide or an oligopeptide, under suitable reaction conditions, to form PPP and recovering the PPP so produced. In this method the tyrosinase and substrate can be contacted in either an aqueous or an organic solvent, where the solvent is preferably methanol, propanol, ethanol or DMSO.

While making PPP it is preferred to use a dipeptide substrate. In addition to varying the substrate to affect the color of the PPP, the color of the PPP produced can be varied by varying the amount of tyrosinase present in said reaction vessel relative to the combined amount of the substrate, or by varying the ratio of the substrate to 1-tyrosine. Where the dipeptide tyr-ala is used, it is preferred to use a ratio of the dipeptide to 1-tyrosine of from 4:1 to 4:10. Where the dipeptide phe-tyr is used, the ratio of the dipeptide to 1-tyrosine is preferably from 5:1 to 1:1.

The invention further contemplates a method for producing PPP comprising the steps of combining PPP with a strong oxidizing agent for a time period selected to produce a PPP having a desired color, and removing the oxidizing agent from the combination. The oxidizing agent is preferably hydrogen peroxide, sodium hypochlorite, potassium permanganate, peracetic acid or perchloric acid. The oxidizing agent is preferably removed from the reaction mixture by ultrafiltration, and ultrafiltration can also be used to fractionate the PPP by using selected molecular weight cut-off filters.

The invention further includes fractionated PPPs which have been recovered using selected molecular weight cut-off filters.

DETAILED DESCRIPTION OF THE INVENTION

Figure 1:
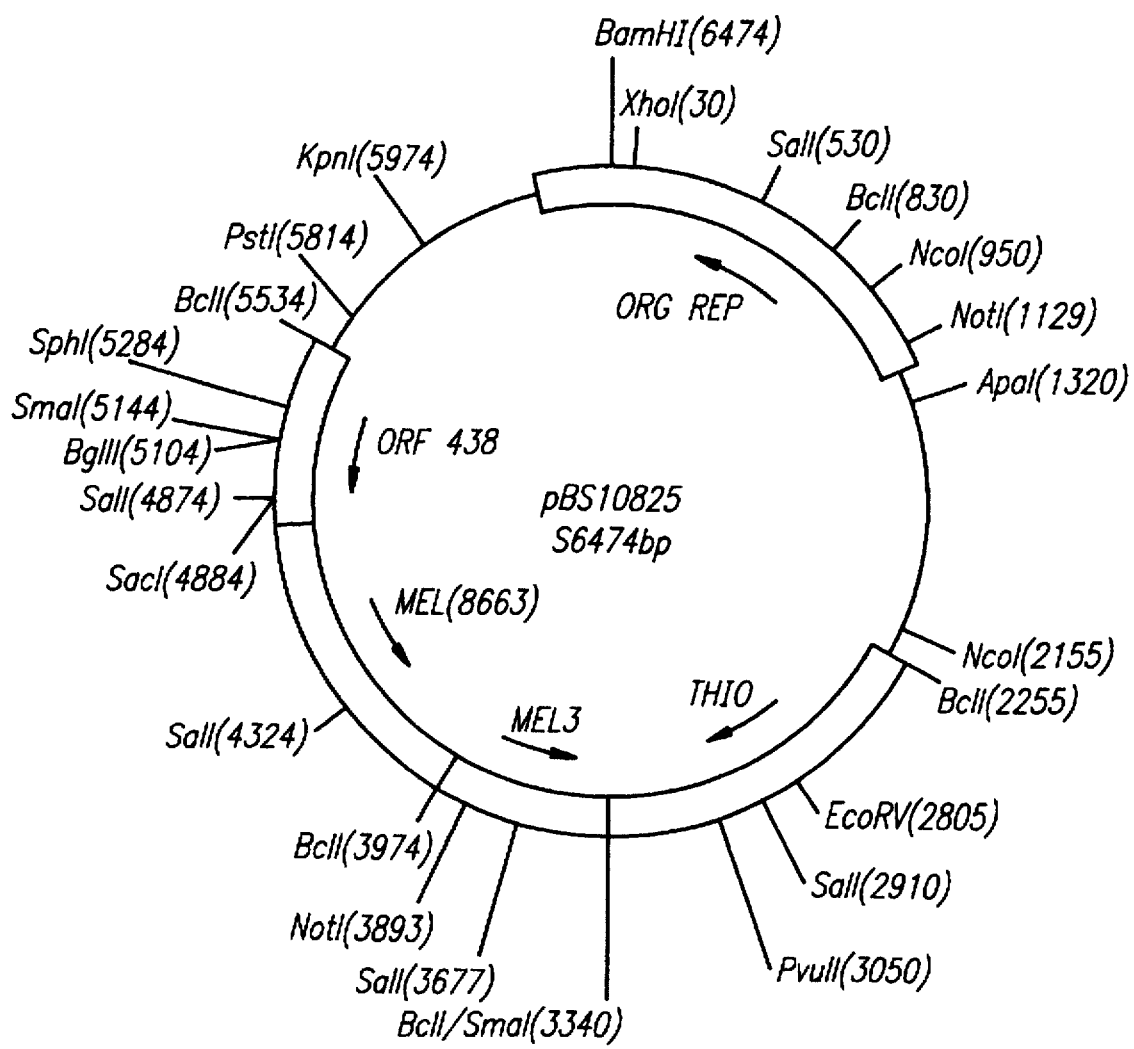
FIG. 1 is the genetic map of plasmid pBS1082S, which is used to transform *Streptomyces antibioticus* according to the invention.

The present invention relates to a process for the in vitro production of chemically modified polyphenolic polymer (PPP). First, stable, highly active extracellular tyrosinase is produced from genetically transformed microorganism such as *Streptomyces antibioticus*. The tyrosinase is then incubated with a reaction substrate such as 1-tyrosine, hydrolyzed protein, or an oligopeptide in combination with 1-tyrosine. The ratio of the oligopeptide/tyrosine combination as well as variation in the concentration of tyrosinase can be used to modify the color, the molecular size, and the spectral absorbance properties of the PPP produced. Alternatively, or additionally, oxidants such as hydrogen peroxide or hypochlorite can be used to modify the color of the PPP, regardless of the method used to produce the PPP, and the PPP can subsequently be fractionated using molecular weight cut-off ultrafiltration. Organic solvents can also be used in the method of making PPP to produce PPPs having variable but reproducible physical properties.

We have found that the physical characteristics of PPP, such as color, may vary with chemical composition. The addition of selected amino acids or peptides to the reaction mixture during synthesis may result in the production of various colors due to their incorporation into the PPP structure. For example, the incorporation of the single amino acid tyrosine will result in a black PPP. The resultant colors can be further modified by chemical oxidation with, but not limited to, hydrogen peroxide or hypochlorite.

PPPs of the present invention have a variety of uses including, but not limited to, protective effect against UV radiation (as a major component in sunscreen products), as antioxidants, as antivirals, as a therapeutic agent to treat neurological disorders, as a protectant for plastics, as a chelator for binding materials such as metals and other compounds, as a coloring agent for foods and hair dyes, and other uses such as in the production of semiconductors.

The present invention will be better understood by reference to the following definitions of the terminology used throughout this specification.

PPPs are polyphenolic polymers having molecular weights ranging from 500 to over a million. They are comprised of a basic phenolic backbone structure which may include phenolic derivatives such as indole. They may also include dipeptides in their structure. The PPPs of the present invention are polymers formed in a reaction catalyzed by tyrosinase or similar enzymes.

Tyrosinase is useful in the production of PPPs such as melanin and for catalysis of biological adhesives, and other uses. Tyrosinase is an enzyme that catalyzes the orthohydroxylation of monophenols to catechols, which is referred to as cresolase activity, and the dehydrogenation of catechols to o-quinones, designated as catecholase activity. Molecular oxygen is used for the hydroxylation reaction. Thus, tyrosinase may also be useful in bioremediation due to its ability to function as an oxidizer and its ability to promote or catalyze such orthohydroxylation and dehydrogenation.

The tyrosinase of the present invention is typically recovered from a cell-free broth which can be further processed by ultra-filtration which results in the concentration of the enzyme and the removal of salts and low molecular weight media and metabolic products. The tyrosinase may be produced by the method of U.S. Ser. Nos. 545,075, filed Jun. 29, 1990, 607,119, filed Nov. 2, 1990, and 857,602, filed Mar. 30, 1992, or by the method of Gardner, et al, supra. The removal of the cellular debris and the ultra-filtration allows for the production of a stable tyrosinase that may be used subsequently in the production of PPPs. Typically the enzyme is stored at −20° C. Alternatively, the enzyme can be freeze dried. Various protectants may be used to stabilize the enzyme such as by the addition of polyhydroxy alcohols such as and most preferably 50% glycerol. The levels of these protectants may range from 5–75% by weight, preferably 35–65%. Storage of the enzyme in an inert gas allows for longer storage and stability of the enzymes.

Numbers can be used to express the color of synthesized PPPs. One method in common usage is the so-called CIE 1976, L*a*b* (pronounced L-star, a-star, b-star) color system wherein the numbers that are used to characterize the colors are defined as follows: L* is called the "value" which is a measure of the lightness or darkness of an object. a* and b* represent hue on two axes, with a* the red-green axis and b* the yellow-blue axis. A full description of this system is described in Billmeyer and Saltzman *Principles of Color Technology*, (2nd ed. 1981), which is hereby incorporated by reference.

Tyrosinase Production

A prerequisite for a large-scale in vitro production of PPPs is the availability of a commercial quantity of a stable, highly active tyrosinase which is subsequently used for the in vitro PPP synthesis. Accordingly the present invention comprises a method for the production of commercial quantities of a stable, highly active tyrosinase from a microorganism, preferably, *Streptomyces antibioticus*. Genetic manipulation involves the transformation of a microorganism with a plasmid or a vector which contains a gene encoding tyrosinase. The transformed microorganism is not only capable of expressing tyrosinase, but also capable of secreting it to the medium. The techniques for the construction of plasmids, vectors and the transformation of the microorganism suitable for the enhancement of tyrosinase production have been described in U.S. patent applications Ser. Nos. 545,075, filed Jun. 29, 1990, 607,119, filed Nov. 2, 1990, and 857,602, filed Mar. 30, 1992, which applications are hereby incorporated by reference. (The corresponding PCT application is WO92/00373, published Jan. 9, 1992.) The spores produced by the transformed *Streptomyces antibioticus* are prepared from ISP4 thiostrepton plates and subsequently inoculated at a concentration of $2.0 \times 10^5$ CFU/liter media, as shown in example 1(a).

Figure 2:
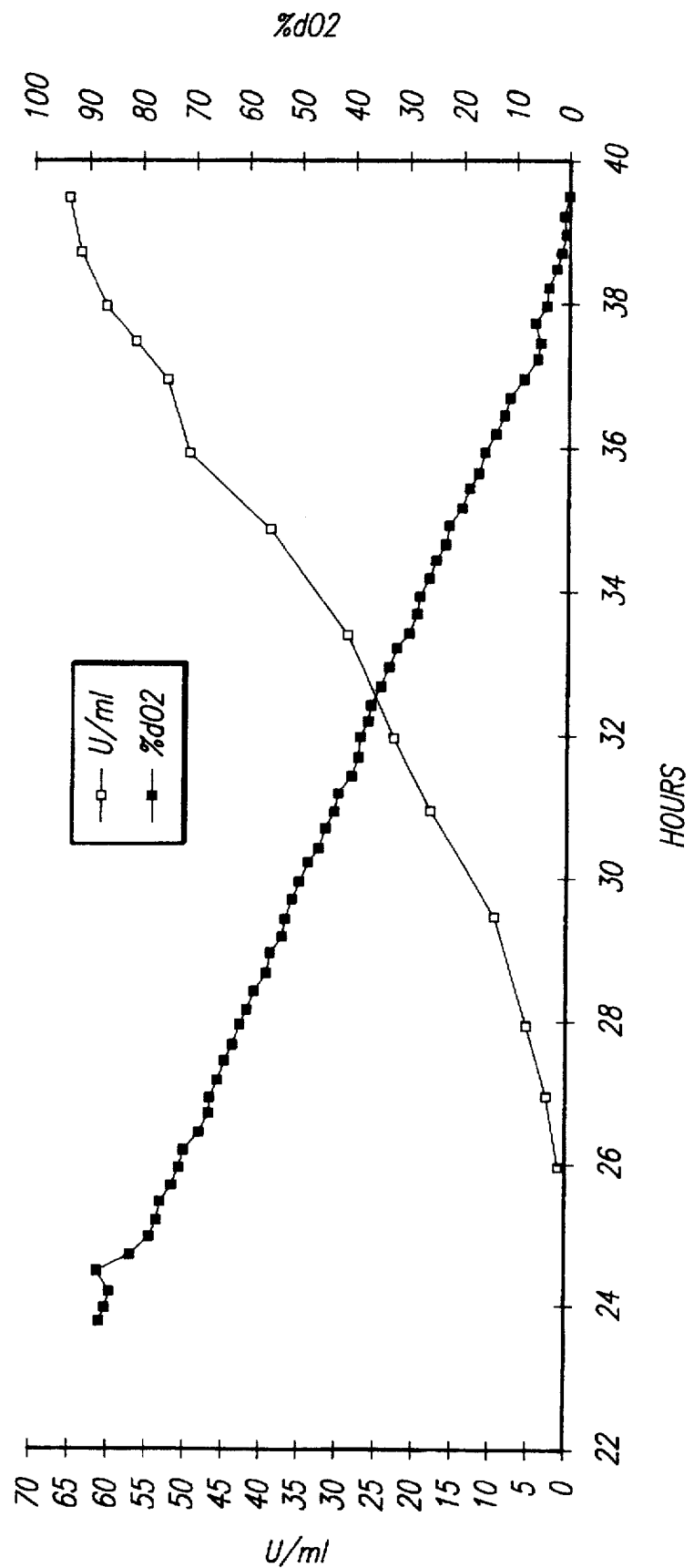
FIG. 2 shows the relationship between tyrosinase yield and the amount of dissolved oxygen in the fermentation process.

One method of increasing the yield of active tyrosinase is to enhance the stability of extracellular tyrosinase after it has been synthesized and secreted by the microorganisms into the media. We have found that our novel low casein media for enzyme production results in a reduced biomass providing a significantly improved, more efficient, enzyme recovery. Applicants have further found that precise control of dissolved oxygen during fermentation results in a increased tyrosinase stability during production (see FIG. 2). The low casein media used for the in vivo production of tyrosinase from the transformed Streptomyces comprises the combinations of appropriate volumes of components provided in example 1(a). Each of the media components is added timely and sequentially to the media to ensure the maximum production of tyrosinase. As can be seen in FIG. 2, a decrease of 5.8% of dissolved oxygen per hour between 24 and 39 hours of the fermentation by adjusting the air flow rate and agitation resulted in the production of 65.9 units/ml tyrosinase. The cells are removed from the broth by filtration and centrifugation and the resultant cell-free broth containing tyrosinase may be used as is or stored at −20° C. until needed for subsequent in vitro PPP synthesis or other uses. The extracellular stable tyrosinase activity is monitored through the fermentation spectrophotometrically by the dopachrome method (Yasunobu, K. T., et al., *J. Biol Chem.* 234: 3291–3205 (1959)). As a consequence of these manipulations, the invention provides a method to produce extracellular, stable tyrosinase at a quantity of over 60 units/ml (see FIG. 2).

Once the tyrosinase is formed, it is stabilized and stored, if desired, for later use. When it is collected as a cell free broth, it can be stored at low temperature, e.g. 4° C. or less and preferably at −20° C. or less. To extend the storage time the broth may be exposed to an inert gas (by sparging to remove air), such as argon. A protectant, such as glycerol can be added to further increase storage time. Alternatively, the tyrosinase can be freeze dried.

EXAMPLE 1(a)

Production of Stable, Highly Active Streptomyces Tyrosinase

*Streptomyces antibioticus* IMRU 3720, obtained from the NRRL, strain (B-16570), was transformed with a constructed plasmid pBS1082S of FIG. 1. Spore stocks were prepared from ISP4 thiostrepton plates (50 mg/ml) as described in Hopwood et al., *Genetic Manipulation of Streptomyces, A Laborabory Manual*, The John Innes Foundation, F. Crowe and Sons Ltd., Norwich, England (1985), the contents of which are incorporated by reference herein.

The spore stock production media used is provided below:

| ISP4 + Thiostrepton Plates | |
|---|---|
| g/liter | |
| 10.0 | Soluble potato starch |
| 1.0 | $K_2HPO_4$ |
| 1.0 | $M_gSO_4.H_2O$ |
| 1.0 | NaCl |
| 2.0 | $(NH_4)_2SO_4$ |
| 2.0 | $CaCO_3$ |

ISP4 + Thiostrepton Plates

| | |
|---|---|
| 20.0 | Agar |
| 0.5 | 1-tyrosine |
| 1.0 ml/liter | Mineral salts |
| 1.0 ml/liter | 0.5% $CuSO_4.5H_2O$ (as below) |
| 1.0 liter | Deionized $H_2O$ |

The media was autoclaved for 20 minutes and then cooled to 50° C. One ml of 50 mg/ml thiostrepton was added into the media. One liter of ISP4+thiostrepton was sufficient to make forty 8.5 cm diameter round petri plates or five 506 $cm^2$ square plates.

The copper sulfate solution used in the above formulation is prepared as follows: One-half gram of $CuSO_4.5H_2O$ is used in 100 ml deionized $H_2O$, and then autoclaved for 20 minutes for spore stocks.

Mineral Salts Solution

| mg/liter | |
|---|---|
| 40 mg | $ZnCl_2$ |
| 200 mg | $FeCl_3.6H_2O$ |
| 10 mg | $CuCl_2.2H_2O$ |
| 10 mg | $MnCl_2.4H_2O$ |
| 10 mg | $Na_2B_4O_7.10H_2O$ |
| 10 mg | $(NH_4)_6Mo_7O_{24}.4H_2O$ |
| 1 liter | Deionized $H_2O$ |

The solution was autoclaved for 20 minutes.

Thiostrepton Stocks

Thiostrepton stocks were prepared by dissolving 50 mg thiostrepton into 1.0 ml DMSO. Antibiotic stocks were stored at −20° C. until needed.

Twenty liters of low casein production media was inoculated with $2.0 \times 10^5$ CFU/liter media in a 30 liter Braun fermentor. The fermentation proceeded at 30° C., 320 rpm and 4.0 liters per minute air flow. An additional 160 g Marcor casein peptone type M in 900 ml water and 6 ml peanut oil was added to the fermentation at 23 hours post inoculation. At 24.5 hours post inoculation, the temperature was reduced from 30° C. to 25° C. At 26 hours post inoculation, 1.0 ml of 5.0% $CuSO_4.5H_2O$ was added to the fermentor. A constant decrease of 5.8% $dO_2$/hr was maintained between 24 and 39 hours of fermentation by adjusting the air flow rate and agitation (see FIG. 2). Extracellular tyrosinase activity was monitored throughout the fermentation spectrophotometrically by the dopachrome method, where unit activity is defined by Lerch and Ettlinger (1972): one unit of tyrosinase will convert one mole of 1-dopa to dopachrome in one minute at 30° C. and pH 6.0. When the extracellular tyrosinase activity stopped increasing at 39.5 hours, (65.9 units/ml), the culture was harvested.

The fermentor was cooled to 17.4° C. Cells were removed from the fermentation broth by filtration through cheese cloth followed by centrifugation with an Alpha Laval centrifuge. The broth was maintained at 4° C. during processing. The cell-free broth can be used for in vitro PPP production and for other uses as is or can be stored at −20° C. for later use.

Copper Sulfate Solution

In the low casein production media, 5 grams of $CuSO_4.5H_2O$ per 100 ml of $H_2O$ is prepared and then autoclaved for 20 minutes.

Low Casein Production Media

| grams/liter | |
|---|---|
| 4.0 g | Marcor Casein Peptone Type M |
| 1.0 g | $KH_2PO_4$ |
| 0.5 g | $MgSO_4.7H_2O$ |
| 1 liter | Deionized $H_2O$ |

Marcor Casein Peptone Type M Addition for 20 Liters

One-hundred sixty grams of Marcor Casein Type M were dissolved in 900 ml deionized $H_2O$, with 6 ml peanut oil and then autoclaved for 35 min.

EXAMPLE 1(b)

Tyrosinase Recovery

Tyrosinase from two 20 liter Braun fermentations was concentrated 25 fold to a 1.2 liter total volume by filtration through a Setec spiral U.F. membrane with a 10,000 molecular weight cutoff. The concentrated tyrosinase was diafiltered 2 times with 2 liters of distilled water and stored at −20° C. until needed in this case for in vitro PPP synthesis.

EXAMPLE 1(c)

Tyrosinase Stabilization

Tyrosinase prepared as in example 1(a) and 1(b) can be stabilized by a variety of techniques. A number of methods were examined and the tyrosinase activity half-life was determined for each storage method (see Table 1). Cell-free broth was stored at different temperatures and in the presence or absence of 50% glycerol. Air was removed from some preparations by sparging the tyrosinase storage container with argon. In addition, ultra-filtered tyrosinase was lyophilized and stored at different temperatures. The tyrosinase half-life activity was determined by periodically sampling each preparation and measuring the remaining tyrosinase activity by the dopachrome method.

TABLE 1

| Enzyme Preparation | Storage Temperature | Tyrosinase Activity Half-Life |
|---|---|---|
| Cell-free broth | −20° C. | >6 Months |
| Cell-free broth | 22° C. | 1 Day |
| Cell-free broth | 4° C. | 23 Days |
| Cell-free broth, Argon | 22° C. | 12 Days |
| Cell-free broth, Argon | 4° C. | 38 Days |
| Cell-free broth 50% Glycerol | 22° C. | 10 Days |
| Cell-free broth 50% Glycerol | 4° C. | 60 Days |
| Cell-free broth 50% Glycerol | −20° C. | >1 Year |
| Cell-free broth 50% Glycerol, Argon | 22° C. | 20 Days |
| Cell-free broth 50% Glycerol, Argon | 4° C. | >1 Year |
| Cell-free broth | −20° C. | >1 Year |

TABLE 1-continued

| Enzyme Preparation | Storage Temperature | Tyrosinase Activity Half-Life |
|---|---|---|
| 50% Glycerol, Argon | | |
| Lyophilized | −20° C. | >1 Year |
| Lyophilized | 22° C. | >1 Year |
| Lyophilized | 37° C. | >1 Year |
| Lyophilized | 45° C. | >1 Year |

PPP Production

Figure 3:
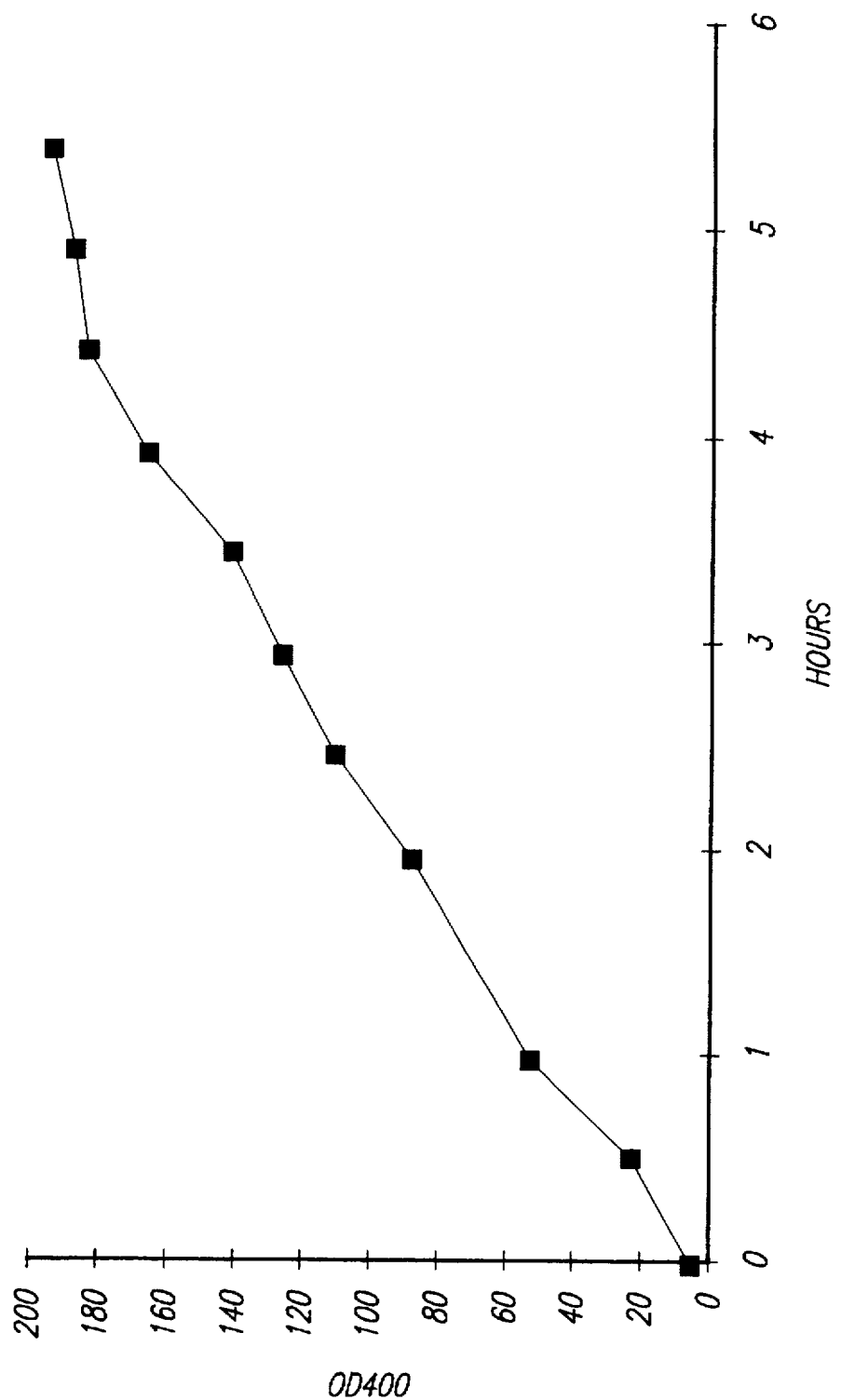
FIG. 3 shows the rate of in vitro PPP production in a 3 liter reaction vessel with rate of synthesis monitored by the increase of absorbance at 400 nm.

The present invention, after achieving a large-scale tyrosinase production, is then directed to a PPP production process without the use of fermentation. To produce PPP the tyrosinase is placed in a buffered aqueous solution and then substrates are added. The PPP production is observed by measuring the optical density (OD) of the reaction mixture at 400 nm ($OD_{400}$) at various intervals of time. The $OD_{400}$ is directly proportional to the concentration of PPP and is monitored to determine the end of the enymatic reaction so that the PPP and their derivatives can be harvested when the OD has leveled off (see FIG. 3). To achieve maximum PPP production, a number of parameters have been explored and taken into consideration. These include: (1) a buffer system in which the tyrosinase exhibits the highest activity; (2) the temperature at which optimum synthesis occurs; (3) the tyrosinase concentration in relation to the amount and type of substrates; (4) the optimum pH for enzymatic reaction; (5) the adequate reaction time; (6) the size of reaction vessel in relation to oxygen exposure; and (7) the amount of dissolved $O_2$ in reaction mixture. The most preferred combination of these parameters, for the substrate L-tyrosine, which gives rise to the production of high levels of PPP has been determined by the applicants and is described in Example 2(a).

The PPP may also be produced using an in vitro enzymatic method in a variety of organic solvents (see Examples 4(a), 4(b) and 4(c)). The tyrosinase is stable and found to be reactive to the added substrates in various organic solvents. The preferred organic solvent system is selected from, but not limited to, the group consisting of methanol, propanol, DMSO, and ethanol.

As described previously, the chemical and physical properties of the PPP produced vary with the composition of substrates and the reaction conditions. Traditionally, the substrates used for PPP production are tyrosine, dopa or their derivatives. In the present invention PPP is produced using tyrosinase mediated polymerization of tyrosine, and/or tyrosine derivatives, and/or tyrosine-containing oligopeptides, including tyrosine dipeptides and/or hydrolyzed proteins. When an oligopeptide is used in combination with 1-tyrosine as the substrate, the color of the resulting PPP can be further modified by varying the ratio of oligopeptides to tyrosine in relation to tyrosinase concentrations. The physical characteristics such as UV absorption spectra, molecular weight, and solubility are also varied with the reaction and with the oligopeptide:tyrosine combination as well as the ratio of such a combination (see Figures (see Examples 3a and 3b) for the variation of UV absorption due to the changes of the combination and the ratio of such combination). Consequently, as illustrated in the following examples the desired physical and/or chemical characteristics of PPP including but not limited to color can be obtained by manipulating: (1) the oligopeptide:tyrosine combination; (2) the ratio of such a combination; (3) the tyrosinase concentration corresponding to each combination; (4) the tyrosinase concentration corresponding to each ratio of one particular combination; (5) reaction conditions; and (6) the solvent system used.

A preferred oligopeptide:tyrosine combination used in the present invention comprises a combination of dipeptide:tyrosine wherein the dipeptide can be a naturally occurring or a chemically modified dipeptide. Through the use of these substrates and 1-tyrosine combinations, it is possible to alter the chemical properties of the PPP as well as the physical properties including the colors of the PPP which include, but are not limited to, red, blue, green, black, brown, orange, violet and yellow.

Chemical Modification Using Oxidants

Chemically changed PPPs can also be obtained by oxidation of the PPPs with an oxidant such as hydrogen peroxide. For example, 1-tyrosine derived PPP (which is black in color) can be modified to a lighter color by hydrogen peroxide (see Example 2b). The final color of PPP is a function of the concentration of hydrogen peroxide used, the length of time the PPP is oxidized, the pH and temperature. Changes in the UV and visible spectra can be used to follow the rate of PPP oxidation and hydrogen peroxide can then be removed by ultrafiltration or passage of the reaction mixture through a catalyst such as platinum.

PPP Analyses

PPPs made by the methods described in the following examples were subjected to some or all of the analytical procedures listed:

(1) UV and visible spectrophotometric scan.
(2) Molecular size determinations via membrane filtration or denaturing agarose electrophoresis.
(3) Color determination via spectrophotometric analysis to obtain L*a*b* values.

EXAMPLE 2(a)

In Vitro Synthesis Production of PPP in Aqueous Solution

L-tyrosine melanin was synthesized in vitro with the *Streptomyces tyrosinase*. A 3.0 L reaction containing 30 g L-tyrosine, 2610 ml 0.05M $Na_2HPO_4$, 260 ml 0.05M $NaH_2PO_4$, pH 8.3, 90 ml ultra-filtered, Streptomyces tyrosinase (40,500 dopachrome units), was performed in a 6.0 L, Wheaton Proteus integral fermenter. The melanin synthesis was carried out at 30° C., 400 RPM, and 1 liters per minute air flow supplemented with 600 ml oxygen per minute. The RPM was increased to 500, at 1 hour. Additional diafiltered tyrosinase was added at 2 hours, (20,250 units), 3.25 hours, (5,400 units), and at 3.5 hours, (20,250 units). A final of 2,880 units tyrosinase per g L-tyrosine was achieved by this enzyme addition scheme. The rate of melanin synthesis was followed by monitoring the increase in absorbance at 400 nm, (see FIG. 3). An average rate of melanin synthesis of 1.76 g melanin/hour was obtained in this reaction (1.0 g melanin is equivalent to 15–20 OD400 units). Melanin synthesis was determined complete at 6 hours when there was no significant increase in the OD400. Melanin was isolated after in vitro synthesis by reducing the reaction mixture to a pH below 4.0 with HCl and recovering the precipitated melanin by centrifugation. Alternatively, the synthesized melanin can be chemically modified directly in the reaction mixture.

EXAMPLE 2(b)

Chemical Modification of In Vitro Synthesized PPP Using Hydrogen Peroxide

PPP produced as in example 2(a) was chemically modified by oxidation with hydrogen peroxide. To 3 L of in vitro synthesized L-tyrosine PPP (in a 6 L Wheaton Proteus integral fermenter), 30% hydrogen peroxide was added until a final concentration of 3.3% hydrogen peroxide was obtained. The PPP was oxidized at 30° C. and 350 RPM. The chemically oxidized PPP was recovered at various time points by acid precipitation, centrifugation and drying. The pH of the oxidized PPP solution was reduced to below pH 2.5 by the addition of concentrated HCl. The acidified PPP was placed at 4° C. for 17 hours to facilitate precipitation. The precipitated PPP was then recovered by centrifugation, 7,000 XG for 10 minutes. Residual amounts of hydrogen peroxide were removed by drying the melanin at 65° C. PPP was removed from the reaction mixture at various times and was analyzed spectrophotometrically. L*a*b* values were determined for each time point (see Table 2).

In the above example, hydrogen peroxide may be removed from the reaction mixture by ultra-filtration through spiral membranes. By choosing the spiral membrane's molecular weight cut-off, not only can the oxidized melanin be concentrated and the hydrogen peroxide removed, but specific size fractions of melanin can be isolated.

TABLE 2

Oxidized PPP L*a*b* values

| Time(hours) | L* | a* | b* |
|---|---|---|---|
| 0 | 84.085 | 1.991 | 5.892 |
| 0.25 | 86.312 | 1.882 | 7.032 |
| 0.5 | 87.969 | 2.222 | 11.986 |
| 1.0 | 88.919 | 2.141 | 12.773 |
| 4.25 | 90.178 | 1.790 | 14.898 |

EXAMPLE 2(c)

Methods of Removal of Hydrogen Peroxide and Recovery of PPP and PPP

Hydrogen peroxide was removed from the PPP and the PPP recovered by using several methods: (1) PPP was acid precipitated by reducing the pH of the reaction mix to 1.5 by the addition of HCl. PPP was then recovered by centrifugation and the remaining hydrogen peroxide was removed by drying the PPP at 70° C.; or (2) hydrogen peroxide was removed from the reaction mixture by ultrafiltration using a 10,000 mw cut-off membrane. The PPP was then recovered by acid precipitation and centrifugation as described in (1); or (3) hydrogen peroxide was removed from the reaction mixture by passage through a platinum coated material. Platinum causes hydrogen peroxide to degrade into water and oxygen. The PPP was then recovered by acid precipitation and centrifugation as described in step (1).

EXAMPLE 2(d)

Chemical Modification of In Vivo Polyphenolic Polymers with $H_2O_2$

Approximately 300 mg of L-tyrosine polyphenolic polymer produced in vivo was suspended in 60 ml of 0.2N $NH_4OH$ containing 1% $H_2O_2$. The solution was incubated, with stirring, at room temperature for one hour. At this point 100 mg of platinum black was added and incubated at room temperature for an additional one hour.

The solution was filtered through a Whatman #1 filter and the pH adjusted to 3.0 with Concentrated HCl. The solution was Centrifuged and the pellet was resuspended in either phosphate buffer at pH 7.0 or in 0.01 n NaOH.

EXAMPLE 2(e)

Larger Scale Chemical Modification of In Vivo PPP with $H_2O_2$

One gram of dried polyphenolic polymer produced in vivo was stirred in 40 ml of 0.1N NaOH for approximately one hour at room temperature. Hydrogen peroxide stock was prepared in 0.2N NaOH for a final concentration of 2%. To the suspended material, 40 ml of 2% $H_2O_2$/0.2N NaOH was added and stirred for 20 minutes at room temperature. Slowly, 7 mg of platinum black was added to the mixture. The solution was then centrifuged at 10,000 rpm for 10 minutes to remove the catalyst. Concentrated HCl was added to the supernatant to adjust the pH to 3.0. The solution was allowed to precipitate for approximately 2 hours at 4° C. After precipitation, the solution was centrifuged at 10,000 rpm for 30 minutes. The precipitated sample was washed three times with 30 ml volumes of acidified distilled water at pH 3.0. Finally, the sample was washed once with 80 ml of 100% acetone and dried.

EXAMPLE 2(f)

Chemical Modification of In Vivo PPP: Removal of $H_2O_2$ via Ultra-filtration Ten grams of dry L-tyrosine polyphenolic polymer, produced in vivo, was suspended in 400 ml of 0.2N $NH_4OH$. To this mixture was added 400 ml of 2% $H_2O_2$ in 0.2N $NH_4OH$ and the solution was stirred for 20 minutes. The pH was adjusted to 5.0 with 1N HCl and centrifuged at 10,000 rpm for 10 minutes. The precipitated impurities were discarded and the supernatant containing the modified PPP was purified by ultra-filtration using a 10,000 molecular weight cut-off membrane. Ultra-filtration continued until no residual hydrogen peroxide was detected. The peroxide free solution was acidified to pH 3.0 with 1N HCl and the PPP was allowed to precipitate for 2 hours at 4° C. and recovered by centrifugation at 10,000 rpm for 20 minutes. The precipitate was washed three times with 800 ml volumes of 0.001 n HCl followed by a wash with 800 ml of 100% acetone. The PPP was then dried in a vacuum oven at 37° C. for approximately 16 hours.

EXAMPLE 3 (a)

In Vitro Production of PPP Using Dipeptides With or Without L-Tyrosine

The purpose of these experiments was to determine the feasibility of producing PPP using dipeptides in combination with l-tyrosine.

Figure 4:
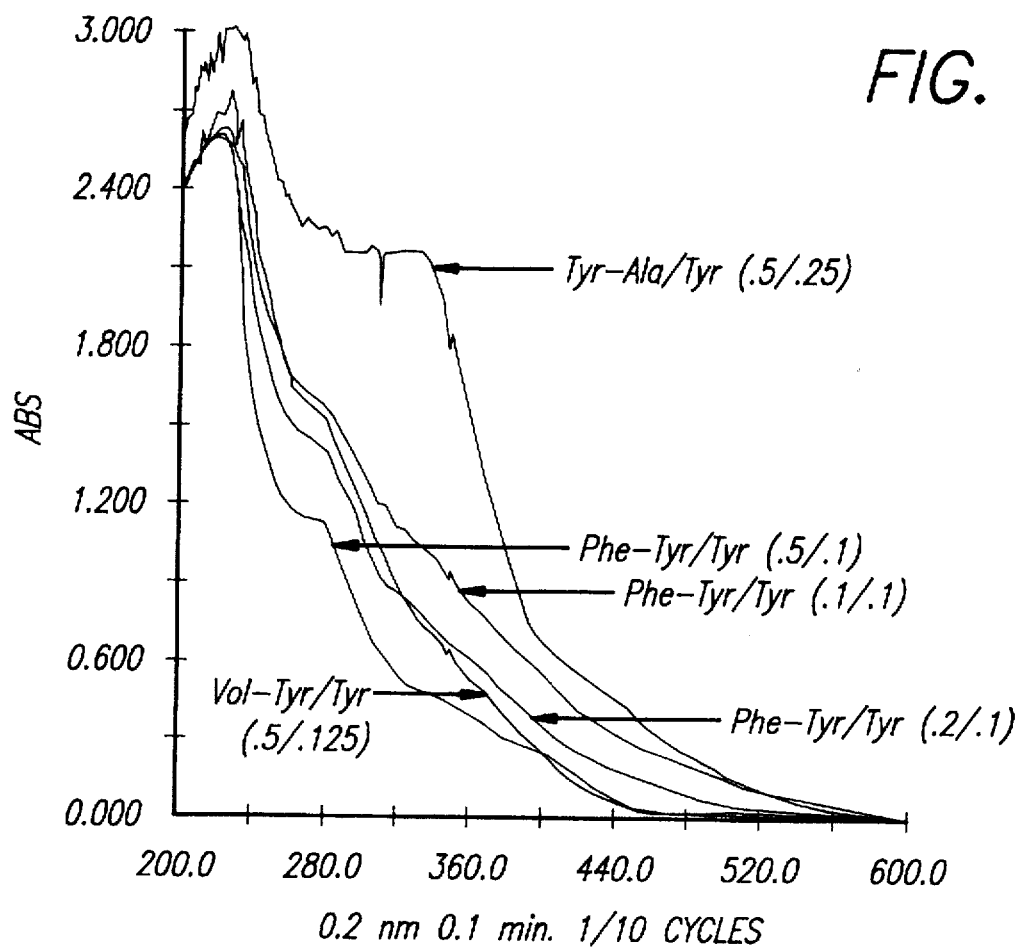
FIG. 4 shows the U.V. absorption spectra for several dipeptide/tyrosine combinations in different ratios.

Procedurally, the detailed experimental steps are described as follows: 500 ml flasks containing 50 ml of 50 mM sodium phosphate buffer, pH 8.0 were prepared. The desired combinations of dipeptide is added to tyrosine, followed by the addition of 250–500 units of Streptomyces tyrosinase enzyme. For example, different PPPs are produced by the present invention wherein the ratios of the substrate/1-tyrosine combination can be described by the following formula: "X/tyr (A/B), wherein (A/B) is the weight ratio between X (the substrate other than 1-tyr) and tyr", and said weight ratio is not required to be kept as a constant for each and every substrate/1-tyrosine combination provided by the present invention. Instead, a preferred embodiment of this invention is to provide a variety of weight ratios for each substrate/1-tyrosine combination. The substrate/1-tyrosine weight ratio combination is selected from, but is not limited to, a group consisting of tyr-ala/tyr (0.1/0.25), tyr-ala/tyr (0.2/0.25), tyr-ala/tyr (0.5/0.25), tyr-ala/tyr (1.0/0.25), phe- tyr/tyr (0.5/0.1), phe-tyr/tyr (0.2/ 0.05), phe-tyr/tyr (0.3/0.1), phe-tyr/tyr (0.2/0.1), and phe-tyr/tyr (0.1/0.1). The flasks are then placed at 25°–30° C. shaking at 300 rpm overnight. The overnight reaction is decanted into 50 ml centrifuge tubes and 0.5 ml of concentrated HCl was added to each tube and mixed. The reaction mixture is allowed to stand at 4° C. for 1–2 hours to completely precipitate the PPP out of the solution. The precipitated material is spun in a table top centrifuge at 3000–4000 rpm for 15 minutes. The supernatant was decanted and the PPP pellet is placed at 70° C. until completely dry, at which point the dry-weight of each sample was determined. Samples were then subjected to further analysis as described previously. The results are shown in Table 3 and FIG. 4. The results shown in Table 3 and FIG. 4 indicate a difference in the quantitative physical characteristic of PPPs made from the same substrate/ tyrosine combination but with different ratios. For example, the molecular weights for the tyr-ala/tyr combination were significantly changed when the ratio of the combination changed from 0.1–0.2/0.25 to 0.5–1.0/0.25. The UV spectrum and the L*a*b* values were also altered when the ratio of the combination was varied. Consequently, different colored PPPs were produced by varying the ratio of the substrate/1-tyrosine combination.

Figure 5:
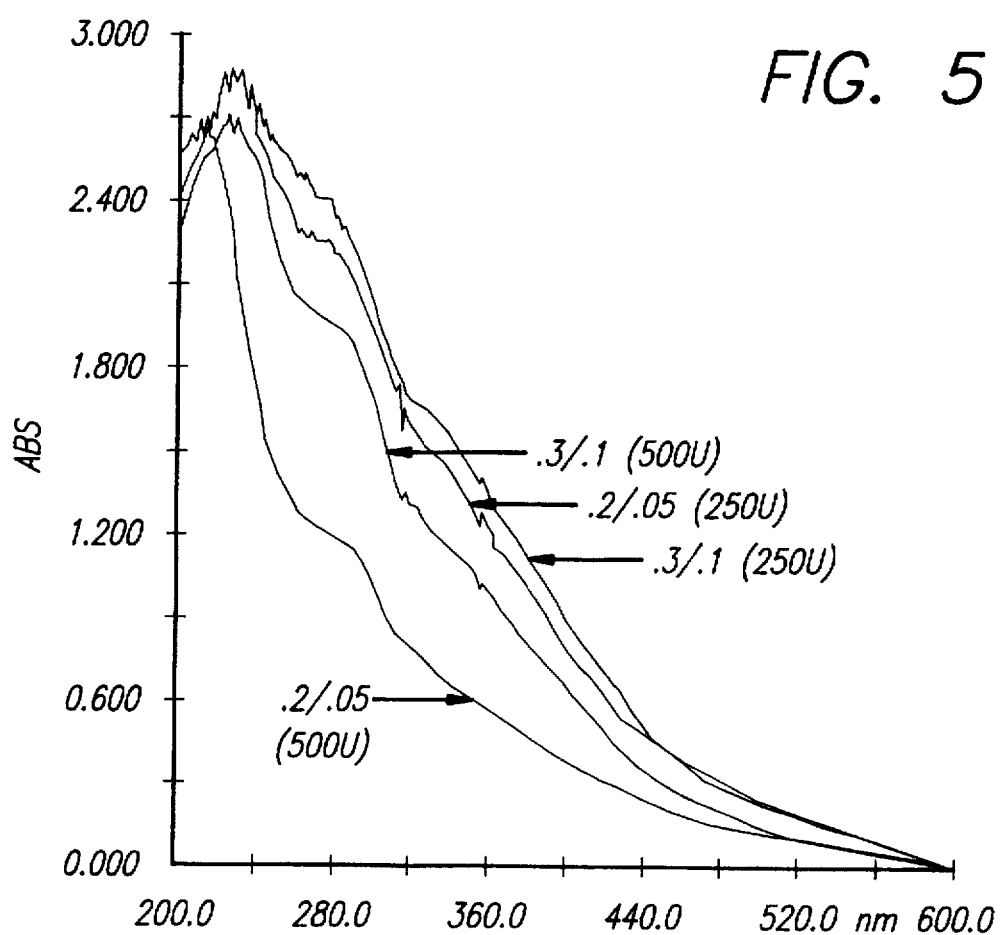
FIG. 5 shows the U.V. spectra of phe-tyr/tyr whose ratios are varied in reference to different concentrations of tyrosinase.

Likewise, as an example, different PPPs are produced from phe-tyr/tyr wherein this combination has different ratios and reacts with different tyrosinase concentrations described by the following formula: "A/B ratio at Y units of tyrosinase". For example, different PPPs are formed by using 0.3/0.1 at 500 units, 0.3/0.1 at 250 units, and 0.2/0.5 at 500 units (FIG. 5 and Table 4).

TABLE 3

| SUBSTRATE | AMT (gms)/ 50 ml | MOL. WEIGHT (DALTONS) | L* | a* | b* |
|---|---|---|---|---|---|
| Tyrosine | 0.25 | Insoluble | 90.903 | 1.119 | 7.557 |
| Tyr-Ala/Tyr | 0.1/0.25 | 30K–200K | 89.625 | 2.094 | 15.835 |
| Tyr-Ala/Tyr | 0.2/0.25 | 14K–200K | 91.841 | 1.568 | 14.576 |
| Tyr-Ala/Tyr | 0.5/0.25 | >3K–30 | 94.104 | 1.022 | 12.629 |
| Tyr-Ala/Tyr | 1.0/0.25 | >3K–14 | 95.458 | 0.457 | 11.251 |
| Phe-Tyr/Tyr | 0.5/0.1 | >3K–14 | 98.739 | −0.076 | 3.391 |
| Phe-Tyr/Tyr | 0.2/0.05 | N.T. | 95.359 | 0.387 | 8.415 |
| Phe-Tyr/Tyr | 0.3/0.1 | N.T. | 97.293 | 0.015 | 6.593 |
| Phe-Tyr/Tyr | 0.2/0.1 | N.T. | 96.821 | 0.139 | 6.845 |
| Phe-Tyr/Tyr | 0.1/0.1 | N.T. | 93.269 | 0.902 | 10.438 |
| Val-Tyr/Tyr | 0.5/0.125 | >3K–22K | 96.35 | 1.353 | 7.382 |

TABLE 4

| SUBSTRATE | Amount g/50 ml | ENZYME [] | REACTION COLOR |
|---|---|---|---|
| PHE-TYR/TYR | .3/.1 | 500 Units | Dark Green |
| PHE-TYR/TYR | .3/.1 | 250 Units | Dark Green |
| PHE-TYR/TYR | .2/.05 | 500 Units | D-Brown/Black |
| PHE-TYR/TYR | .2/.05 | 250 Units | D-Green/Brown |

EXAMPLE 3(b)

In Vitro Production of PPP via the Addition of Dipeptides with Naturally Occurring and/or Biochemically/Chemically Modified Amino Acids The results shown in Table 5 indicate that different dipeptides were useful substrates for the production of PPP with distinct physical properties, for example, reproducible colors. This is true whether the dipeptides consisted of naturally occurring amino acids, chemically modified amino acids, or a combination. The constituents of PPP determined the molecular weight, solubility, yield, UV spectrum, cost of production and the ultimate colors of the PPPs. It is noted that black PPPs were produced when a variety of hydrolyzed proteins, instead of oligopeptides, were used as the substrates.

TABLE 5

| SUBSTRATE | GRAMS/ 50 ml | REACTION COLOR | MOL WEIGHT |
|---|---|---|---|
| Tyrosine | .25 | Black | |
| Tyr-Ala | .05 | Brown | |
| Tyr-Ala | 1 | Brown | >3000–14000 |
| Tyr-Ala/Tyr | .05/.25 | Dark-Brown | |
| Tyr-Ala/Tyr | .1/.25 | Dark-Brown | 30000–>200000 |
| Tyr-Ala/Tyr | .2/.25 | Dark-Brown | 14000–200000 |
| Tyr-Ala/Tyr | .5/.25 | Dark-Brown | >3000–30000 |
| Tyr-Ala/Tyr | 1/.25 | Dark-Brown | >3000–14000 |
| Val-Tyr/Tyr | .5/1.25 | Red Brown | >3000–22000 |
| N-Acetyl-L-Cysteine/Tyr | .5/.1 | Yellow | |
| N-Acetyl-L-Tyrosine/Tyr | .5/.1 | Red Brown | >3000–30000 |
| Glycyl-L-Tyrosine/Tyr | .5/.1 | Red Brown | 14000–>200000 |
| Phe-Tyr/Tyr | .5/.1 | Green | >3000–14000 |
| Ala-Tyr/Tyr | .5/.1 | Brown | |
| L-Tyrosine Methyl Ester/Tyr | .5/.1 | Yellow | |
| L-Tyrosine Ethyl Ester/Tyr | .5/.1 | Yellow | |
| 5-Hydroxydopamine/Tyr | .5/.2 | Dark-Brown | |
| L-3-Methoxy Tyrosine/Tyr | .5/.2 | Black | 22000–>200000 |
| N-Acetylglycine/Tyr | .5/.2 | Black | |
| L-Tyrosine Allyl Ester/Tyr | .5/.2 | Yellow | |
| 3-Amino-L-Tyrosine/Tyr | .5/.2 | Yellow | |
| Catachol/Tyr | .5/.2 | Grey Black | |
| 3-Iodo-L-Tyrosine/Tyr | .5/.2 | Black | |
| Tyr-Tyr/Tyr | .5/.2 | Dark-Brown | 30000–>200000 |
| 6-Hydroxydopamine/Tyr | .5/.2 | Black | |
| L-Tyrosine Hydrazide/Tyr | .5/.2 | Dark-Brown | |
| DL-M-Tyrosine/Tyr | .5/.2 | Black | |
| N-Chloroacetyl-L-Tyrosine/Tyr | .5/.2 | Red Brown | >3000–<14000 |
| L-α-Methyl Dopa/Tyr | .5/.2 | Black | |
| Chlorogenic Acid/Tyr | .4/.2 | Black | |
| N-Acetyl-L-Tyrosinamide/Tyr | .2/.1 | Black | 30000–>200000 |
| Poly-L-Tyrosine/Tyr | .2/.1 | Black | |
| Trp-Tyr/Tyr | .13/.05 | Black | |
| L-β-3,4-Dihydroxyphe. Ala.Met.Ester/Tyr | .12/05 | Yellow-Brown | |
| Tyr-Gly/Tyr | .07/.05 | Black | 22000–>200000 |
| Silk Protein/Tyr | .5/.5 | Black | 10000–100000 |
| Silk Protein/Tyr | 1/.5 | Black | 10000–50000 |
| Silk Protein/Tyr | 1.5/.5 | Black | <10000–46000 |
| Silk Protein/Tyr | 2/.5 | Black | <10000–40000 |

TABLE 5-continued

| SUBSTRATE | GRAMS/ 50 ml | REACTION COLOR | MOL WEIGHT |
|---|---|---|---|
| Silk Protein/Tyr | 2.5/.5 | Black | <10000–30000 |
| Silk Protein/Tyr | 3/.5 | Black | <10000–30000 |
| Wheat Protein/Tyr | 1/.5 | Black | 30000–>200000 |
| Soy Protein/Tyr | 1/.5 | Black | <3,000–200000 |

EXAMPLE 4(a)

Production of PPP in Organic Solvent

The in vitro synthesis of PPP via Streptomyces tyrosinase in organic solvent systems was empirically studied. A selection of solvents and their concentrations in aqueous buffer was established for reactivity with tyrosinase.

One ml reactions were conducted with varying concentrations of solvents, to which tyrosinase enzyme and substrate (1-dopa or 1-tyrosine) were added to determine reactivity. As shown in the following Table 6, tyrosinase was found to be reactive with 1-dopa and 1-tyrosine in a variety of organic solvents such as methanol, ethanol, DMSO and propanol. The maximum enzyme reactivity was observed for solvent concentrations between 50–70%.

TABLE 6

| 1 | A SOLVENT | B % [ ] | C L-DOPA REACTIVITY | D L-TYROSINASE REACTIVITY |
|---|---|---|---|---|
| 2 | Methanol | 50 | ++++ | +++ |
| 3 |  | 70 | +++ | ++ |
| 4 |  | 90 | + | — |
| 5 |  | 100 | — | — |
| 6 | Propanol | 50 | ++++ | +++ |
| 7 |  | 70 | ++++ | +++ |
| 8 |  | 90 | +++ | + |
| 9 |  | 100 | — | — |
| 10 | DMSO | 50 | +++ | + |
| 11 |  | 70 | — | — |
| 12 | Ethanol | 50 | ++++ | +++ |
| 13 |  | 70 | ++++ | ++ |
| 14 |  | 90 | ++ | — |
| 15 |  | 100 | — | — |

In Table 6 a "dash" (—) symbol indicates no apparent reactivity. The "plus" (+) symbols indicate visible reactivity between substrate and tyrosinase. Thus going from lightly tinted (+) to black PPP (++++).

EXAMPLE 4(b)

In Vitro Production of Polyphenolic Polymers in Organic Solvents

The following example describes steps followed to enzymatically produce L-tyrosine polyphenolic polymers in ethanol.

A two liter erlenmeyer flask containing 1.5 liters of 25 mM NaPO$_4$ buffer, pH 7.0/40% ethanol was prepared. An amount of 7.5 grams of L-tyrosine was added to the flask for a final concentration of 0.5%. The enzyme tyrosinase (38,000 units) was added and the whole mixture was placed in an incubator at 25°–30° C. and shaken at 300 rpm for approximately 48 hours.

Upon completion of incubation unincorporated L-tyrosine was removed by passing the solution first through Whatman #1 filter and then through a 0.8 μm filter. Concentrated hydrochloric acid was added to the filtrate to adjust the pH to 1.0. The solution was placed at 4° C. overnight and then was centrifuged at 7,000 rpm for approximately 15 minutes. At this point two species of polyphenolic polymers were isolated: an acid precipitable and an acid soluble fraction. The acid soluble fraction (supernatant) was decanted into a 4 liter beaker with a large bottom surface area for efficient drying. Both the acid precipitable and soluble fractions were then placed at 70° C. and dried.

Further sample preparation of the dried, acid soluble fraction was performed to obtain two additional and distinct species of polyphenolic polymers. The dried acid soluble fraction was resuspended in approximately 50 ml of 50 mM NaPO$_4$ buffer at pH 8.0. The pH of the solution was then adjusted with NaOH to pH 7.0. At pH 7.0, a brown/tan precipitate was formed. The mixture was centrifuged at 4,000 rpm for 15 minutes and separated into two fractions, a precipitate and a soluble fraction.

EXAMPLE 4(c)

In vitro Production and Oxidation of PPP in Organic Solvents

An in vitro enzymatic PPP synthesis was conducted as follows: One liter flasks were prepared which contained either 500 ml of 50% ethanol in 25 mM sodium phosphate buffer at pH 8.0 or 500 ml of 25 mM sodium phosphate buffer at pH 8.0. To each flask was added 1% L-tyrosine and 10,000 units of tyrosinase. The flasks were then placed on a shaker at 30° C. and 300 rpm for 3 hours. The pH of each flask was adjusted to 9.0 by the addition of NaOH. Hydrogen peroxide was added to the reaction mixtures so that its final concentration was 2%. The flasks were stirred at room temperature for 3.5 hours. Aliquots of 25 ml were removed at various time points for analysis. The pH of the reaction mixtures were adjusted to 2.0 with HCl which precipitated the modified PPPs. After storage at 4° C. overnight, the mixtures were centrifuged and the resulting PPPs were dried and characterized as shown below in Table 7.

TABLE 6

|  | 50% ETOH | CONTROL |
|---|---|---|
| Molecular Size: (Reaction Time) |  |  |
| t = 0 | insoluble | insoluble |
| t = 15 min | 50K–<10K | >200K–>10K |
| t = 3.5 hours | 50K–<10K (much lighter) | 100K–<10K |
| Dry Yield: (per 500 mls) |  |  |
| t = 0 | 0.4 gms | 1.4 gms |
| t = 15 min | 0.2 gms | n.d. |
| t = 3.5 hours | 0.1 gms | 0.7 gms |

*Streptomyces antibioticus* incorporating the plasmid pBS1082S shown in FIG. 1 of this application deposited at the American Type Culture Collection (ATCC), Rockville, Md., USA, on Nov. 25, 1992 under the terms of the Budapest Treaty on the International Recognition of the Deposit of Microorganisms for the Purposes of Patent Procedure and Regulations thereunder (Budapest Treaty) and is thus maintained and made available according to the terms of the Budapest Treaty. Availability of this culture is not to be construed as a license to practice the invention in contravention of the rights granted under the authority of any government in accordance with its patent laws.

The deposited culture has been assigned ATCC deposit number 69132.

While the invention has been disclosed by reference to the details of preferred embodiments, the disclosure is intended to be illustrative rather than limiting, as it is contemplated that modifications will readily occur to those skilled in the art, within the spirit of the invention and the scope of the appended claims.

We claim:

1. A microbial culture, comprising:
   a) at least about 10 units of stabilized tyrosinase activity per ml; and
   b) a microorganism that has produced said tyrosinase activity selected from the group consisting of Escherichia, Streptomyces, Bacillus, Streptococcus, Salmonella, Staphylococcus, and Vibrio, wherein said microorganism contains an expression vector with polynucleotides encoding tyrosinase, and wherein said tyrosinase activity has been stabilized by reducing the amount of dissolved oxygen present in the medium during tyrosinase expression.

2. The culture of claim 1, wherein said microorganism contains a plasmid comprising a nucleotide sequence substantially similar to the ORF438 and MEL encoding region of plasmid pBS1082S.

3. The culture of claim 1, wherein said microorganism expresses said tyrosinase while said dissolved oxygen is reduced at a rate of about 5.8% per hour.

4. A microbial culture, comprising:
   a) active extracellular tyrosinase at a concentration of at least about 10 units/ml; and
   b) *S. antibioticus* transformed with an expression vector containing polynucleotides encoding tyrosinase, wherein said *S. antibioticus* is grown on a medium consisting essentially of casein hydrolysate as a nitrogen source, and wherein said *S. antibioticus* produces said tyrosinase while the dissolved oxygen is reduced at a rate of about 5.8% per hour.

5. The culture of claim 1 wherein the concentration of extracellular tyrosinase activity in the growth medium is between about 10 units/ml and about 60 units/ml.

6. The culture of claim 4 wherein the concentration of extracellular tyrosinase activity in the growth medium is between about 10 units/ml and about 60 units/ml.

* * * * *